(12) United States Patent
Hoyme et al.

(10) Patent No.: US 7,460,912 B2
(45) Date of Patent: Dec. 2, 2008

(54) SYSTEM AND METHOD FOR TEMPORARY PROGRAMMING FOR IMPLANTED MEDICAL DEVICES

(75) Inventors: Kenneth P. Hoyme, Plymouth, MN (US); Alan H. Smythe, White Bear Lake, MN (US); Howard D. Simms, Jr., Shoreview, MN (US); Conrad L. Sowder, Minneapolis, MN (US); David Ternes, Roseville, MN (US); Sylvia Quiles, Edina, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 553 days.

(21) Appl. No.: 10/993,699

(22) Filed: Nov. 19, 2004

(65) Prior Publication Data

US 2006/0111759 A1 May 25, 2006

(51) Int. Cl.
*A61N 1/362* (2006.01)
(52) U.S. Cl. ..................................... 607/59
(58) Field of Classification Search ............. 607/28–30, 607/59
See application file for complete search history.

(56) References Cited

U.S. PATENT DOCUMENTS 4,253,466 A   3/1981  Hartlaub et al.
4,515,160 A   5/1985  Keimel
5,456,692 A   10/1995 Smith, Jr. et al.
7,212,863 B2  5/2007  Strandberg
2001/0037220 A1  11/2001  Merry et al.
2006/0030904 A1  2/2006  Quiles

FOREIGN PATENT DOCUMENTS

WO   WO-2006055131 A1   5/2006

OTHER PUBLICATIONS

"International Search Report and Written Opinion for Application No. PCT/US2005/036811, date mailed Mar. 20, 2006", 15 Pages.

*Primary Examiner*—Scott M. Getzow
(74) *Attorney, Agent, or Firm*—Schwegman, Lundberg & Woessner, P.A.

(57) ABSTRACT

A system and method for temporary programming of an implantable medical device. The system and method include a repeater uploading temporary programming and instructions to a temporary memory of the device and then instructing the device to operate according to the temporary instructions. If during a first time period, the device is not in continuous periodic communication with the repeater, the device automatically reverts to operation under the normal operating instructions. At the end of the first time period, the caregiver or the patient may decide to revert to the normal programming. During a second time period, the device operates according to the temporary programming unless the caregiver or the patient instructs the device to revert to the normal programming, or the device fails to receive a periodic continuation signal from the repeater. Adverse health affects to the patient may also trigger the device to revert to the normal programming during either the first or second time period.

57 Claims, 5 Drawing Sheets

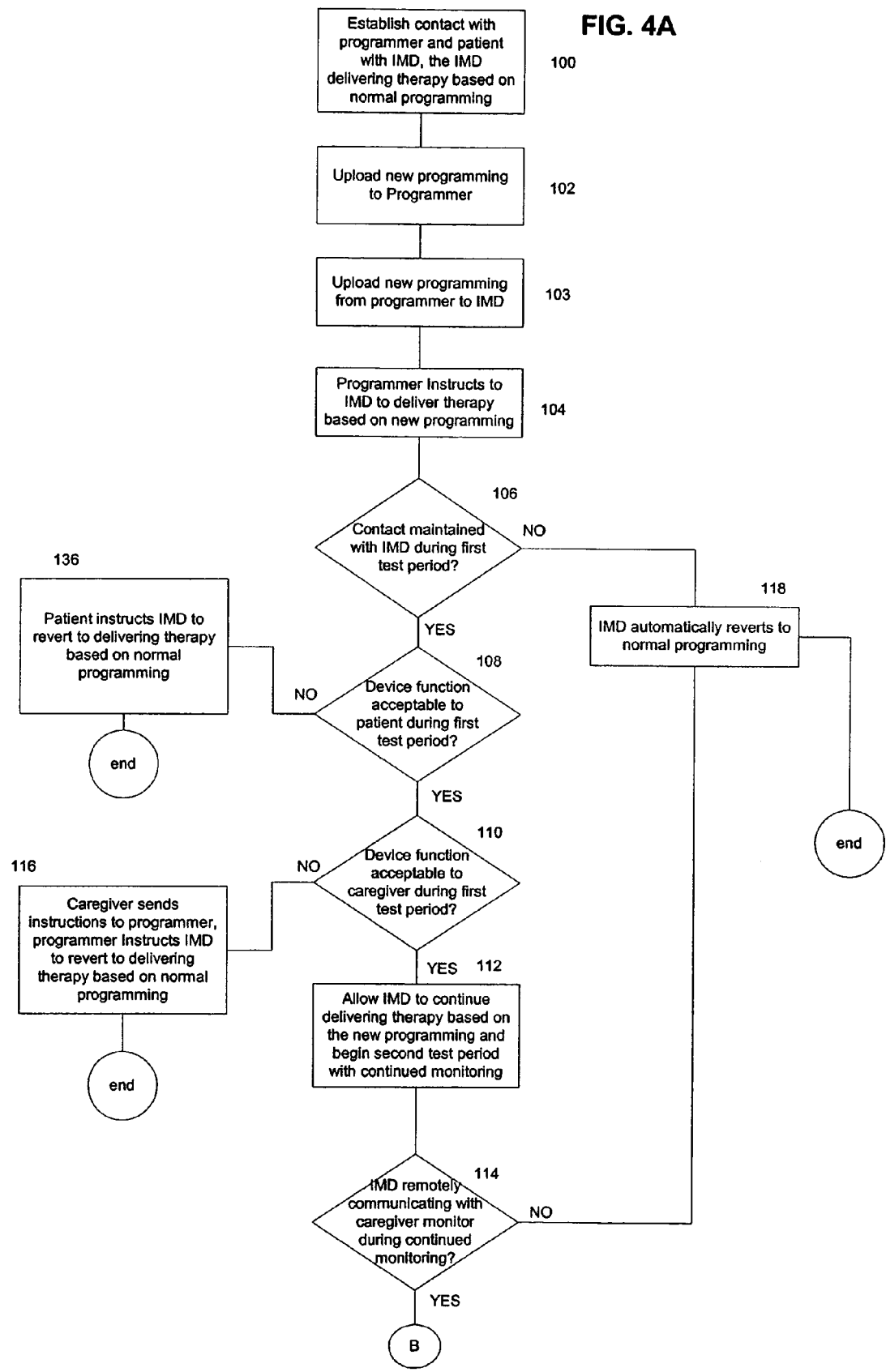

SYSTEM AND METHOD FOR TEMPORARY PROGRAMMING FOR IMPLANTED MEDICAL DEVICES

TECHNICAL FIELD

The present invention generally relates to implanted medical devices and external repeaters. More specifically, the present invention relates to devices and methods for temporary programming of implanted medical devices.

BACKGROUND

Current medical technology utilizes a number of implanted medical devices to provide a wide-range of therapy for patients. Such implanted medical devices (IMDs) may provide rhythm altering electrical impulses to a patient's heart or other types and forms of electrical or neuro-muscular stimulus. These IMDs may also infuse a variety of therapeutic agents. Many of these IMDs are implanted beneath the skin of a patient and frequent physical access to the devices for alteration of the intensity, duration or other characteristics of the therapy is not desirable.

Current technology in the medical device industry allows for monitoring and communication with an implanted medical device without needing to directly access the IMD. Such access may even be accomplished remotely with telemetry tools capable of transmitting and receiving information via existing long-distance communication avenues, such as telephone, cellular communications or radio links. While these known techniques do permit remote alteration of the therapy delivered by an IMD, additional safety measures to guard against mistakes in the programming of the new therapy or unexpected consequences of application of the new therapy are desirable.

Operation of an IMD based on a set of proposed or temporary operating parameters is also currently known. However, the current technology requires that a patient be physically present at a caregiver's location and within local telemetry range of the caregiver's programming equipment. In addition, once proper loading of the temporary parameters into the IMD has been verified, and IMD operation based on the temporary parameters has been verified, the caregiver's programming equipment is required to instruct the IMD to adopt the temporary parameters as normal operating parameters. Current IMD only permit operation in a temporary parameter mode when the IMD is proximate to and in continuous communication with the caregiver's programming equipment.

SUMMARY

The present invention relates to a system for programming an implanted medical device. The system includes a medical device configured to be implanted within in a body of a patient. The medical device includes electrical circuitry to provide treatment to the patient, a first digital storage area for holding normal operation instructions and settings, a second digital storage area for holding temporary operating instructions and settings, a communications subsystem and a timing subsystem. The system also includes a repeater external of the patient's body, the repeater including a communication subsystem configured to communicate with the communications subsystem of the medical device.

The implanted medical device is configured to provide therapy to the patient using the normal operation instructions and settings stored in the first digital storage area. The repeater is configured to transmit temporary operation instructions and settings to the medical device for storage in the second digital storage area. The medical device may be instructed by the repeater to use the temporary operating instructions and settings to provide therapy to the patient. After the medical device has begun providing therapy using the temporary operation instructions and settings, the medical device will revert to the normal operation instructions and settings if a continuation signal is not received from the repeater within a first predetermined period of time.

The present invention further relates to a method of providing therapy to a patient with a programmable implantable device. The method includes providing the patient, the programmable implantable device and an external repeater remotely located from a caregiver treating the patient. The device delivers therapy to the patient based on normal operating instructions stored on the device. The caregiver communicates temporary operating instructions to the repeater. The repeater communicates the temporary operating instructions to the device and the device storing the temporary instructions in memory. The repeater communicates with the device to begin delivering therapy to the patient based on the temporary instructions. The device reverts to delivering therapy to the patient based on the normal instructions if the device does not maintain continuous periodic communication with repeater for a first predetermined period of time.

BRIEF DESCRIPTION OF THE DRAWINGS

The accompanying drawings, which are incorporated in and constitute a part of the description, illustrate several aspects of the invention and together with the detailed description, serve to explain the principles of the invention. A brief description of the drawings is as follows:

FIGS. 4A and 4B are a flow chart of an alternative process for programming the implantable medical device of FIG. 2 with temporary operating instructions.

DETAILED DESCRIPTION OF THE PREFERRED EMBODIMENT

Reference will now be made in detail to exemplary aspects of the present invention which are illustrated in the accompanying drawings. Wherever possible, the same reference numbers will be used throughout the drawings to refer to the same or like parts.

Figure 1:
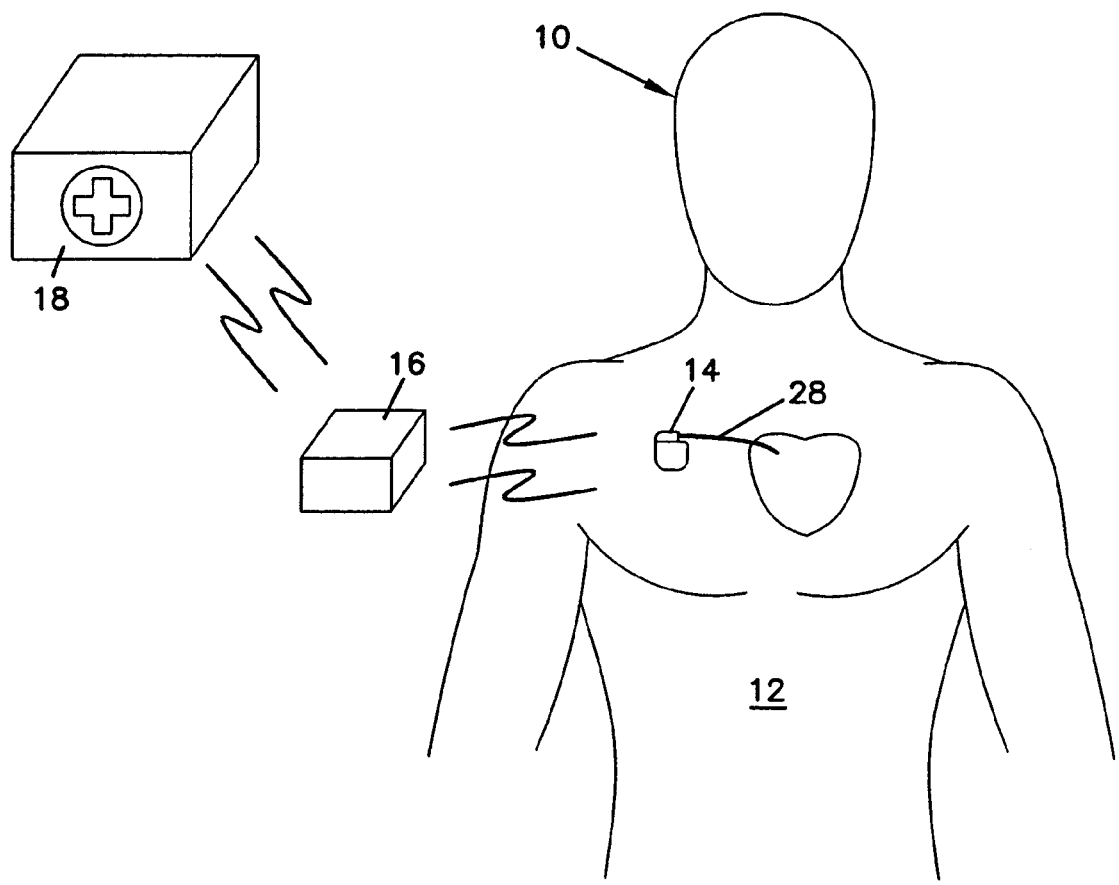
FIG. 1 is a schematic view of an implantable medical device implanted within a patient's body, a repeater in proximity of the body to communicate with the device and a physician at a caregiver facility located remotely from the device and the repeater communicating with the repeater.

FIG. 1 shows a patient 10 within whose body 12 is implanted an implantable medical device 14 (shown as a cardiac rhythm management device) to provide therapy to the patient. The device includes communication circuitry to permit wireless communication with an external repeater 16. Repeater 16 may provide operating instructions to device 14 and may receive data from device 14 regarding therapy provided by device 14. Repeater 16 may also collect data from device 14 regarding the reaction of patient 10 to the therapy being provided by device 14.

Also shown in FIG. 1 is a caregiver facility 18. Caregivers at facility 18 may provide instructions to and receive information from repeater 16. While a caregiver at such a facility is preferably a physician who is treating patient 10 and familiar with the health situation of patient 10, the caregiver may also be a specialist in the particular device implanted in patient 10 who is working in conjunction with the patient's physician. It is anticipated that device 14 could include devices providing electrical impulses to some portion of a patient's body (such as defibrillators or pacemakers) or may deliver therapeutic agents (such as infusion pumps). While the actions performed by the device may differ depending on the application and medical condition being treated, the functions and features described below for altering therapy instructions or parameters are applicable to any similar implanted medical devices (IMDs). The caregiver may be using a programming device at the facility to develop and store instructions to be uploaded to repeater 16 for transmission to device 14. The programming device may also receive information from device 14 through repeater 16 to permit the caregiver to review and analyze the patient's response to therapy.

If the caregiver and patient 10 are both located at caregiver facility 18, the programming device may be integral with the repeater.

Figure 2:
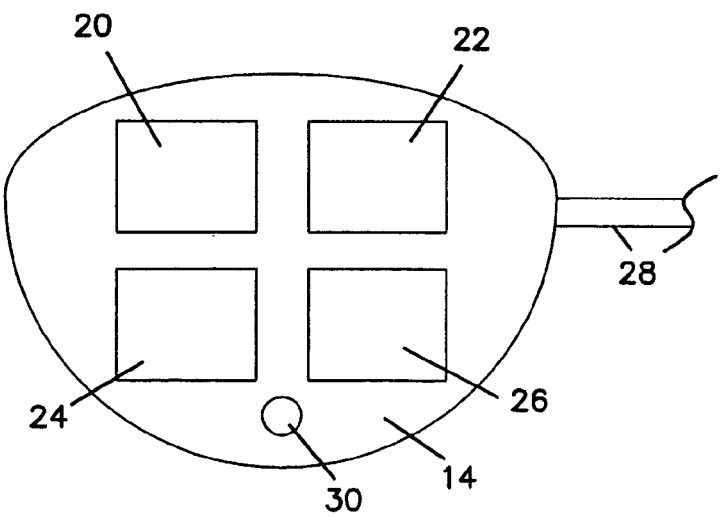
FIG. 2 is a schematic view of the implantable medical device of FIG. 1.

Referring now to FIG. 2, device 14 includes a communication subsystem 20 and a therapy delivery subsystem 22. Therapy delivery subsystem 22 via a conduit 28 to the portion of patient 10's body 12 where therapy is desired. In the example shown above in FIG. 1, conduit 28 is an electrical lead connecting device 14 (a pacemaker) to the patient's heart. Therapy delivery subsystem 22 may also include a patient status sensing capability which allows device 14 to sense and record particular elements of patient 10's condition which might be affected by the therapy delivered by device 14. For example, subsystem 22 of the pacemaker of FIG. 1 may collect and record data on heart rhythm which may be used to determine if different therapy protocols may be desirable for patient 10. In another example, if device 14 were an infusion pump for delivering insulin, subsystem 22 may collect and record blood sugar levels.

Device 14 also may include an on-board memory 24 for storing and maintaining normal programming, such as operating instructions and parameters, on which the normal therapy provided to the patient is based. Normal memory 24 may also be referred to as permanent memory, although, as will be discussed below, memory 24 may be subject to being overwritten with new instructions and parameters of operation to alter the therapy provided to patient 10 by device 14. Device 14 may also include a temporary on-board memory 26 for storing and maintaining new or temporary programming, such as operating instructions and parameters, for delivering therapy to patient 10. Within device 14 may be a switch 30 which is able to toggle operation of device 14 between the two different sets of operating instructions and parameters that may be stored in memories 24 and 26. Switch 30 may be a virtual or software switch which is operable based on instructions received by device 14 through repeater 16, or based on programming within device 14. Alternatively, switch 30 may also include a physical magnetic switch actuated by patient 10, or the caregiver or another person adjacent patient 10 using a magnetic wand.

Figure 3A:
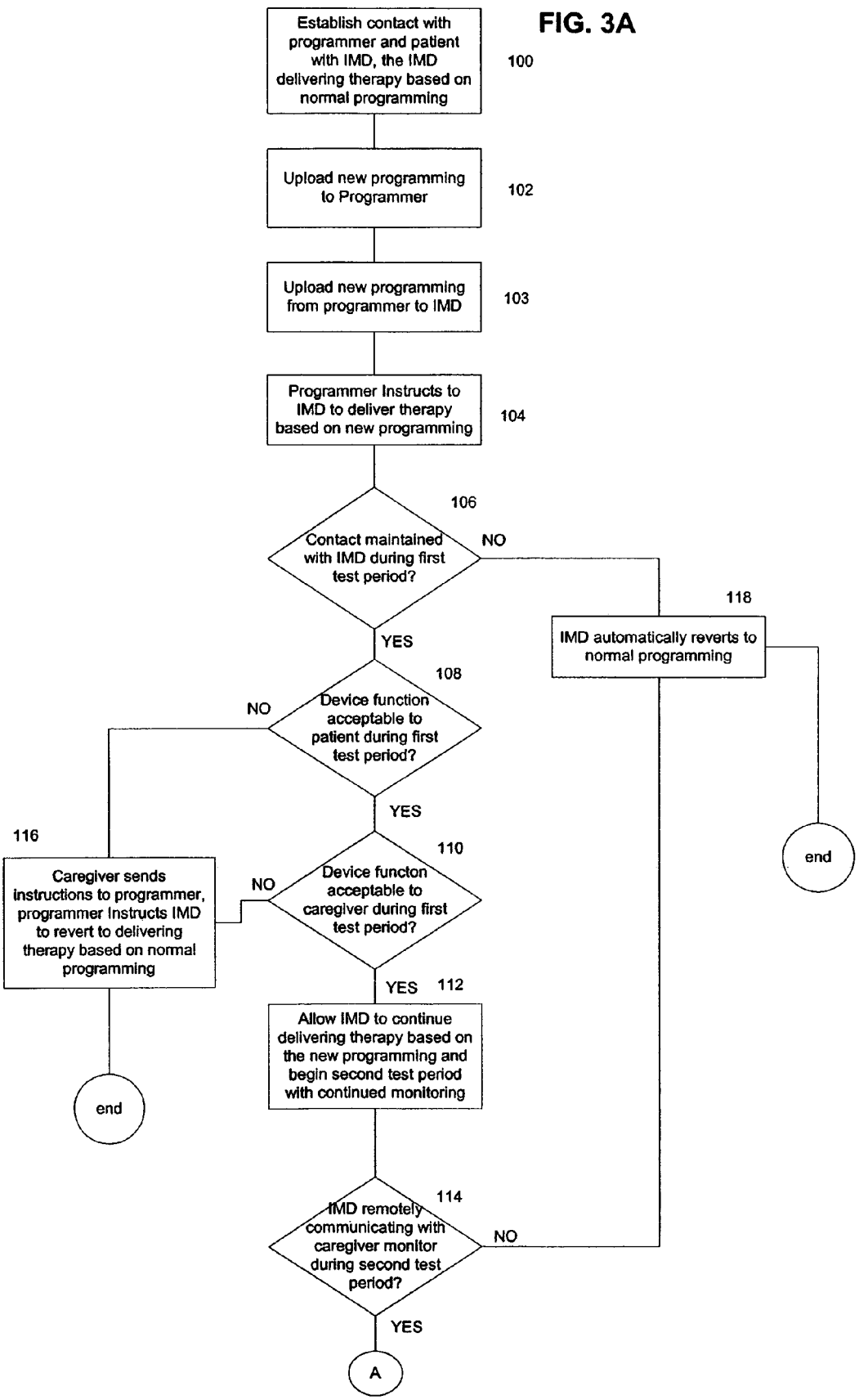
FIGS. 3A and 3B are a flow chart of a process for programming the implantable medical device of FIG. 2 with temporary operating instructions.
Figure 3B:
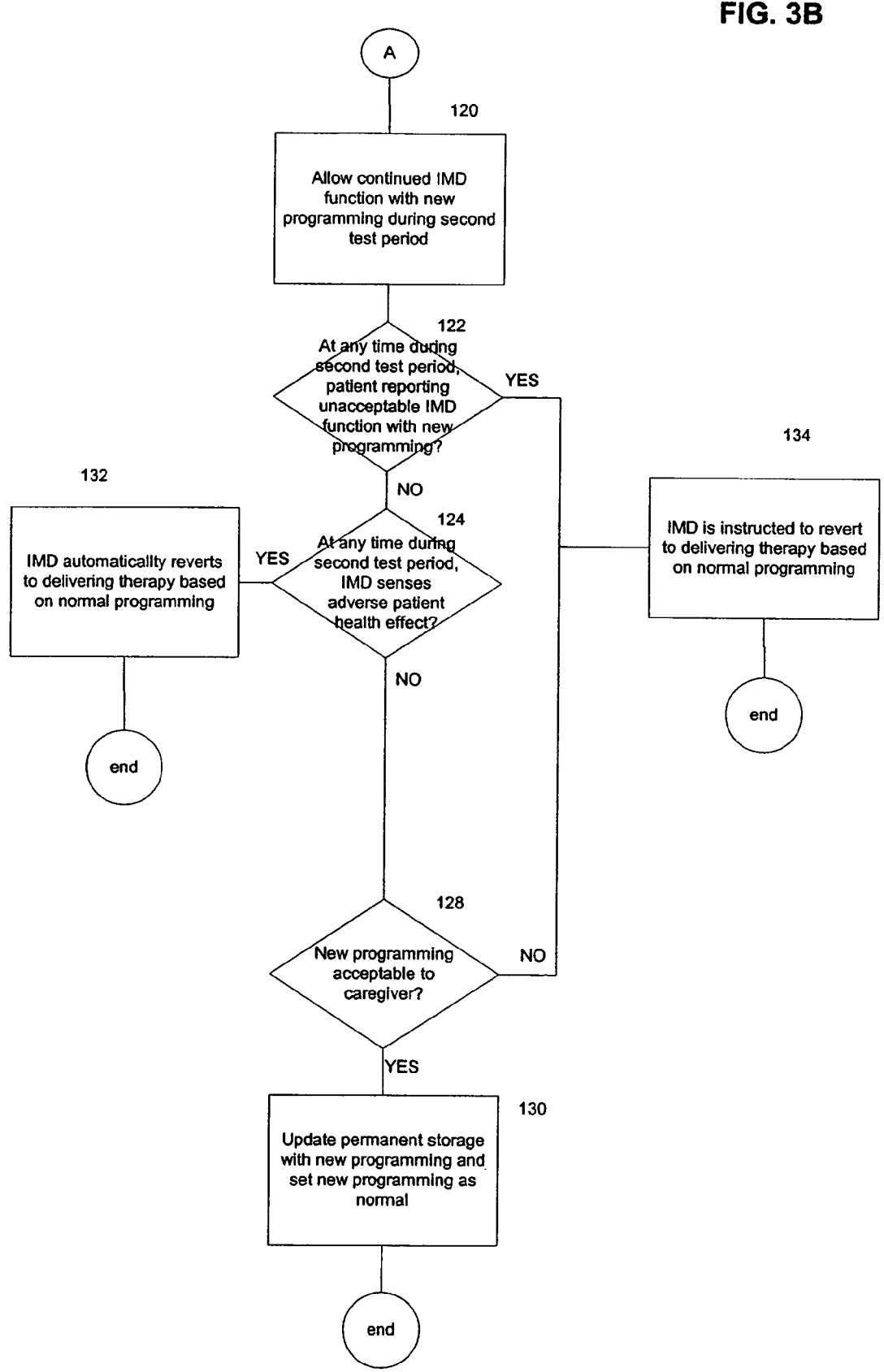

Referring now to FIGS. 3A and 3B, uploading and testing of new operating instructions to device 14 includes a number of guards to prevent detrimental effects to patient 10 caused by alterations of the programming of device 10. While it is known to have a patient schedule an office visit with their caregiver to change or adjust the programming of the instructions used by an implanted medical device, such as device 10, such office visits are sometimes not possible or may be impractical or inconvenient. Remote programming of medical devices is also known as possible, but has not been a viable approach due to a lack of appropriate and necessary safeguards to protect against mistakes in reprogramming and/or new programming which does not have the desired effect on the patient's health. The procedures laid out in FIGS. 3A and 3B illustrates one embodiment of remote programming of IMDs including adequate patient safeguards to permit secure and safe programming alterations.

To initiate the installation and testing of new programming for an IMD, patient 10 is in close proximity with repeater 16 so that repeater 16 may transmit signals to and receive signals from the IMD or device 14. Device 14 is delivering therapy to patient 10 based on a set of normal programming of instructions stored in memory 24 on-board device 14. At 100, the caregiver is located remotely from patient 10 and repeater 16 and establishes communication with the repeater and patient 10 to begin the loading and testing of new programming for device 14. "Remotely located" is defined to mean the caregiver and the patient (along with the IMD and the repeater) are not located at the same physical location. For example, the caregiver may be a physician at a hospital and the patient may be located at his or her home. On the other end of the spectrum, a patient (along with the IMD and the repeater) and caregiver located in the same room or treatment bay are not considered to be remotely located with respect to each other. The caregiver then uploads new programming to repeater 16 for communication to device 14 at 102. The new programming is then transferred from repeater 16 to device 14, which in turn stores the new programming in memory 26 on-board device 14 for temporary storage at 103.

Once the new programming has been uploaded from repeater 16 to device 14 and stored in memory 26, the caregiver, through repeater 16, instructs device 14 to begin delivering therapy to patient 10 based on the new programming for a first test period at 104. The first test period is relatively short (preferably ranging from a few seconds to a few minutes) to determine if there are any immediate ill effects to the health of patient 10. The first test period, at a minimum must extend long enough to verify that the new programming has been fully and correctly uploaded to memory 26. The first test period also may extend long enough to collect data regarding certain parameters of heart function and patient reaction to the new programming. The first test period may further extend to permit a caregiver to access the data regarding the certain parameters of heart function and patient reaction to the new programming via remote communication between repeater 16 and caregiver facility 18, so that the caregiver can verify that the new programming is initially functioning adequately.

During this first test period, at 106, patient 10 may remain within the immediate vicinity of repeater 16 so that repeater 16 is receiving a generally continuous stream of data regarding patient 10's reaction to the new therapy regime. The nature of the communication stream may be periodic, with polling and response required at certain regular intervals, and still be continuous communication as referred to herein. Such a continuous, periodic stream of communication enables device 14 to conserve battery life during the process. At 118, device 14 is configured at this stage to automatically revert to the prior normal programming if patient 10 moves away from the immediate vicinity of repeater 16. Thus, if patient 10 has a strong negative reaction to the new programming and collapses or falls away from repeater 16, device 14 will discontinue use of the new programming. As a safety measure, it is desirable that patient 10 remain near repeater 16 for the first test period so that data regarding the function of device 14 in response to the new programming can be verified. If patient 10 moves away from repeater 16 prior to completion of this first test period, device 14 will revert to the normal programming, even if no ill effects of the new programming have been detected.

During the first test period and once the first test period has been completed, the patient may be given an opportunity to critique the new programming of device 14 and the effect that therapy based on this new programming may have had upon the patient's perceived health and quality of life, at 108. If the patient's perception is that the therapy delivered by device 14 degrades comfort, interferes with the patient's normal daily activities, or otherwise has a deleterious impact on the patient, at 116, device 14 may be instructed to revert to providing therapy based on the normal programming held by memory 24. At 110, during the first test period and upon completion of the first test period, the caregiver may review the function of device 14 at 108 to determine if the new programming results in the desired function of device 14 and the desired response to the new therapy is detected in patient 10. If the caregiver determines that the level of function of device 14 is not having the desired results with regard to the patient's health, the caregiver may also, at 116, direct device 14 to revert back to providing therapy based on the normal programming within memory 24. At 116, the instruction to device 14 to revert to therapy based on the normal programming is communicated through repeater 16 by the caregiver in consultation with patient 10. Alternatively, repeater 16 may include a button, switch or other feature permitting patient 10 to provide the instruction to device 14 to revert to normal programming within memory 24.

The uploading of new programming and temporary operation of device 14 during the first test period have been described as remote from caregiver location 18. It is anticipated that the uploading new programming and the first test period could also occur at caregiver location 18.

If the patient and caregiver concur that the function of device 14 and the patient's response to the function of device based on the new programming are adequate and desirable, device 14 can be instructed to operate for a second test period, at 112. During this second test period, patient 10 and device 14 would not necessarily need to remain directly adjacent to repeater 16, as required during the first test period. During the second test period, patient 10 may be ambulatory and would only need to periodically return to the proximity of repeater 16 so that repeater 16 can download information from device 14 to monitor function of device 14. Patient 10 may need to have the repeater 16 query device 14 one or several times a day. Repeater 16 may then communicate the status information from device 14 and possibly from patient 10 regarding function of device 14 back to the caregiver. Device 14 may include a function which records when the periodic transfer of information from device 14 to repeater 16 occurs. If too great of a time gap exists since the last transfer, device 14 may be programmed to automatically revert to delivering therapy based on the normal programming in memory 24, at 118. The limit on the acceptable time gap prior to reversion to therapy delivery based on normal programming may be varied to meet the particular needs and circumstances of the patient.

Provided that repeater 16 and device 14 remain in periodic communication, the operation of device 14 delivering therapy based on the new programming is allowed to continue for the duration of the second test period, at 120. Upon completion of the second test period, at 122, patient 10 is again queried as the effectiveness and desirability of therapy based on the new programming. At this point or at any time during the second test period, if the patient finds the therapy produces undesirable results, the patient may request that device 14 be instructed by repeater 16 to revert to therapy delivery based on the normal programming. At 124, device 14 may be recording data regarding the health parameters of patient 10 which indicate the current or future health of the patient may be adversely affected, as compared to desirable or acceptable health parameters programmed into device 14. If such adverse effects are sensed and/or recorded by device 14, device 14 may be programmed to automatically revert to delivering therapy based on the normal programming, at 132. Alternatively, repeater 16 may provide the analysis tools required to verify if the parameters sensed by device 14 are within pre-programmed acceptable parameters. If the parameters are determined by repeater 16 to be outside of an acceptable range, device 14 may be programmed to revert automatically to delivering therapy based on the normal programming, at 132.

At the completion of the second test period, or at any time during the second test period, the caregiver may also determine that the therapy delivered based on the new programming is acceptable or unacceptable, at 128. At the completion of the second test period or at any time during the second test period, if the caregiver decides that the therapy based on the new programming is not acceptable, at 134, the caregiver may communicate instructions to device 14 through repeater 16 to revert to delivering therapy based on the normal programming in memory 24. Alternatively, repeater 16 may include a button, switch or other feature permitting patient 10 to provide the instruction to device 14 to revert to normal programming within memory 24. Alternatively, patient 10 may be provided with a separate device, such as a hand-held device, to revert IMD to function according to the normal programming within memory 24.

If the caregiver determines the new programming and the therapy delivered based on the new programming are acceptable, at 130, device 14 may be instructed to write the new programming into memory 24, over-writing the existing normal programming. Once written into memory 24, the new programming can be relabeled the normal programming, and device 14 can deliver therapy based on the programming newly written in memory 24 without additional contact with repeater 16 being required.

Figure 4B:
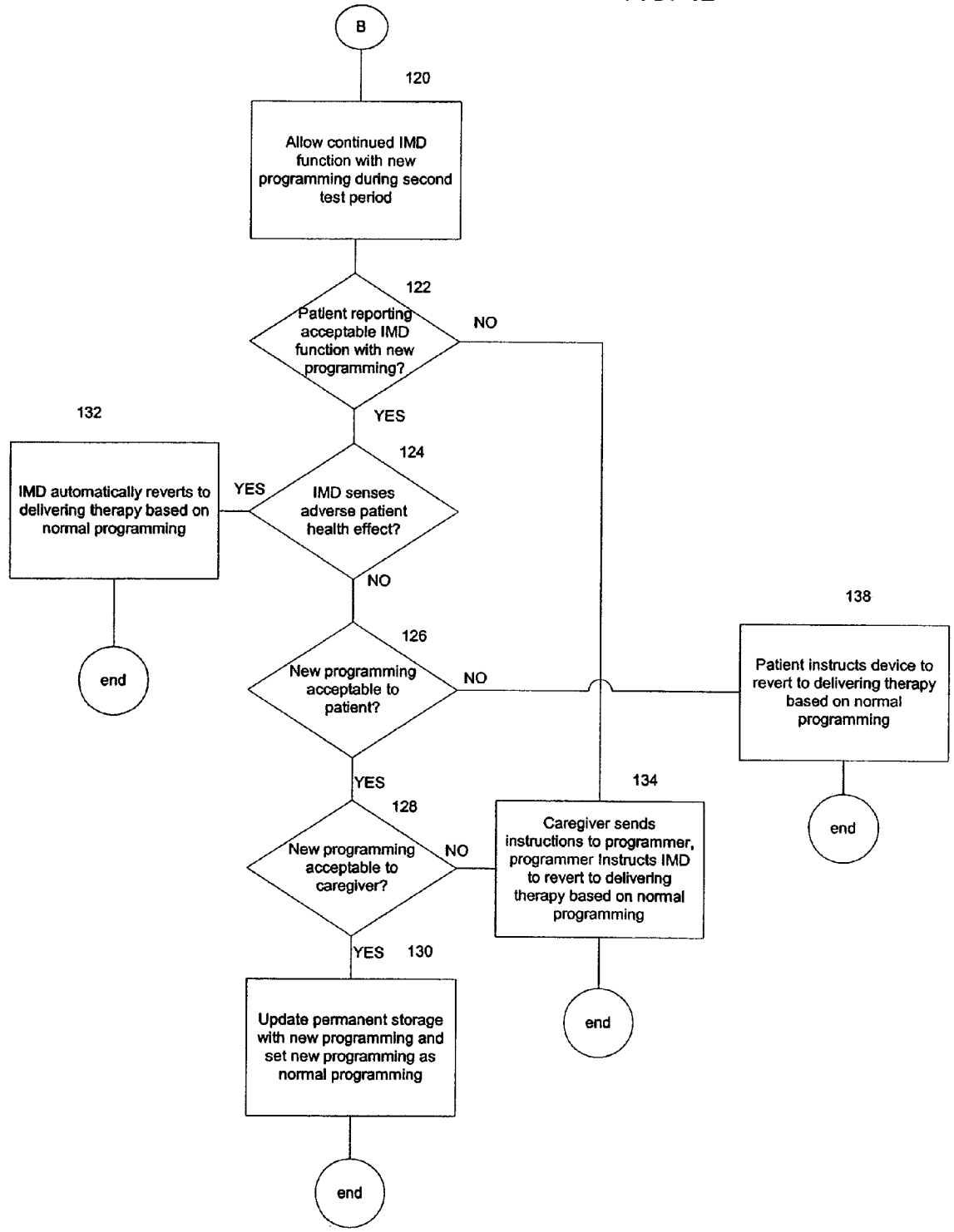

FIGS. 4A and 4B illustrate the uploading and testing of the delivery of therapy by device 14 based on new programming. The process of FIGS. 4A and 4B is similar to the process detailed above, with regard to FIGS. 3A and 3B, with device 14 including a patient actuable switch 30 for reverting device 14 to therapy delivery based on the normal programming. At 108, if patient 10 determines that the therapy delivery based on the new programming is not acceptable, patient 10 may, at 136, deliver instructions to device 14 directly to revert to therapy based on the normal programming. Patient 10 need not involve the caregiver in the reversion. Instructions to device 14 from patient 10 may be delivered by actuation of switch 30.

In FIG. 4B, during and following the second test period, the patient may also take the initiative to revert device 14 to delivering therapy based on the normal programming, at 126 and 138. Patient 10 may still report acceptable or non-acceptable function of device 14 at 122 and the caregiver may send instructions to revert device 14 to delivering therapy based on the normal programming. However, patient 10 may still have the ability to revert device 14 to normal programming, at 138. Instructions to device 14 from patient 10 may be delivered by actuation of switch 30.

The embodiments of the inventions disclosed herein have been discussed for the purpose of familiarizing the reader with novel aspects of the present invention. Although preferred embodiments have been shown and described, many changes, modifications, and substitutions may be made by one having skill in the art without unnecessarily departing from the spirit and scope of the present invention. Having described preferred aspects and embodiments of the present invention, modifications and equivalents of the disclosed concepts may readily occur to one skilled in the art. However, it is intended that such modifications and equivalents be included within the scope of the claims which are appended hereto.

What is claimed is:

1. A system for programming an implanted medical device comprising:
   a medical device configured to be implanted within in a body of a patient;
   the medical device including electrical circuitry to provide treatment to the patient, a first digital storage area for holding normal operation instructions and settings, a second digital storage area for holding temporary operating instructions and settings, a communications subsystem and a timing subsystem;
   a repeater external of the patient's body, the repeater including a communication subsystem configured to communicate with the communications subsystem of the medical device and with a programming device;
   the patient, the medical device and the repeater remotely located from the programming device;
   the medical device configured to provide therapy to the patient using the normal operation instructions and settings stored in the first digital storage area;
   the repeater configured to transmit temporary operation instructions and settings to the medical device for storage in the second digital storage area;
   the repeater configured to instruct the medical device to use the temporary operating instructions and settings to deliver therapy to the patient;
   wherein upon receiving from the repeater the instruction to use the temporary operating instructions and settings to deliver therapy to the patient, the medical device initiates a first predetermined period of time during which the medical device begins delivering therapy using the temporary operation instructions and settings, and wherein the medical device will revert to the normal operation instructions and settings if the medical device fails to receive a continuation signal from the repeater within a first time interval during the first predetermined period of time; and
   wherein upon completion of the first predetermined period of time without reverting to normal operation, the medical device initiates a second predetermined period of time during which the medical device is configured to revert to the normal operation instructions and settings if the medical device fails to receive a continuation signal from the repeater within a second time interval during the second predetermined period of time, wherein the second time interval is longer than the first time interval.

2. The system of claim 1, wherein the periodic continuation signal received from the repeater during a second predetermined period of time includes a request to transfer device function information from the medical device.

3. The system of claim 2, wherein the patient is ambulatory during the second predetermined period of time.

4. The system of claim 1, wherein the device is configured to replace the normal operation instructions with the temporary operation instructions and normally deliver therapy to the patient based on the formerly temporary operation instructions after the second predetermined period of time.

5. The system of claim 1, wherein the device is configured to revert to delivery of therapy to the patient based on the normal operation instructions after the second predetermined period of time, unless instructed to replace the normal operation instructions with the temporary operation instructions and normally deliver therapy to the patient based on the formerly temporary operation instructions.

6. The system of claim 1, wherein the repeater is configured to signal the device to replace the normal instructions with the temporary operation instructions and normally deliver therapy to the patient based on the formerly temporary operation instructions.

7. The system of claim 1, wherein the repeater is configured to signal to the device to revert to delivery of therapy to the patient based on the normal operation instructions, and remove the temporary operation instructions from the second digital storage area.

8. The system of claim 1, wherein the device is configured to sense patient response to the therapy based on the temporary operation instructions and revert to delivering therapy based on the normal operation instructions if the device senses an adverse response to the therapy based on the temporary operation instructions.

9. The system of claim 1, wherein the device is configured to sense patient response to the therapy based on the temporary operation instructions and, if the response is acceptable, to replace the normal instructions with the temporary operation instructions and normally deliver therapy to the patient based on the formerly temporary operation instructions.

10. The system of claim 1, wherein the repeater is configured to receive data from the device regarding patient response to therapy delivered based on the temporary operation instructions and communicating to the device to revert to delivering therapy based on the normal operation instructions if the patient response to therapy based on the temporary operation instructions is adverse.

11. The system of claim 1, wherein the repeater is configured to receive data from the device regarding patient response to therapy delivered based on the temporary operation instructions and, if the response is acceptable, to signal the device to replace the normal instructions with the temporary operation instructions and normally deliver therapy to the patient based on the formerly temporary operation instructions.

12. The system of claim 1, wherein the device is configured to respond to the patient signaling the device by reverting to delivering therapy based on the normal operation instructions if the temporary operation instructions do not provide acceptable patient response.

13. The system of claim 12, wherein the patient signals the device to revert to delivering therapy based on the normal operation instructions using a magnet.

14. The system of claim 12, wherein the patient signals the device to revert to delivering therapy based on the normal operation instructions using an electronic wand.

15. The system of claim 1, wherein the device is configured to respond to the patient signaling the device by replacing the normal operation instructions with the temporary operation instructions and normally delivering therapy to the patient based on the formerly temporary operation instructions.

16. The system of claim 15, wherein the patient signals the device to replace the normal instructions with the temporary operation instructions and normally deliver therapy to the patient based on the formerly temporary operation instructions using a magnet.

17. The system of claim 15, wherein the patient signals the device to replace the normal instructions with the temporary operation instructions and normally deliver therapy to the patient based on the formerly temporary operation instructions using an electronic wand.

18. The system of claim 1, wherein the device is configured to respond to the caregiver signaling the device by reverting to delivering therapy based on the normal operation instructions if the temporary operation instructions do not provide acceptable patient response.

19. The system of claim 18, wherein the caregiver signals the device to revert to delivering therapy based on the normal operation instructions using a magnet.

20. The system of claim 18, wherein the caregiver signals the device to revert to delivering therapy based on the normal operation instructions using an electronic wand.

21. A method of providing therapy to a patient with a programmable implantable medical device, the method comprising:

providing the programmable implantable medical device and an external repeater remotely located from a caregiver facility, the device delivering therapy to the patient based on normal operating instructions stored in a first memory of the device, the repeater to communicate with a programming device;

the programming device at the caregiver facility communicating temporary operating instructions to the repeater;

the repeater communicating the temporary operating instructions to the device, and the device storing the temporary operating instructions in a second memory;

the repeater communicating with the device to begin delivering therapy to the patient based on the temporary operating instructions during a first predetermined period of time initiated by the device upon receiving from the repeater an instruction to use the temporary operating instructions and settings to deliver therapy to the patient;

the device reverting to delivering therapy to the patient based on the normal operating instructions if the device does not receive a continuation signal from the repeater within a first time interval during the first predetermined period of time;

the device initiating a second predetermined upon completion of the first predetermined period of time without reverting to normal operation; and the device reverting to delivery of therapy to the patient based on the normal operation instructions if the device fails to receive a continuation signal from the repeater within a second time interval during the second predetermined period of time following the first predetermined period of time, wherein the second time interval is longer than the first time interval.

22. The method of claim 21, wherein the device reverting during the second predetermined time period includes the device reverting to delivering therapy to the patient based on the normal operating instructions if the device does not receive a request to transfer device function information from the medical device to the repeater within a second predetermined period of time.

23. The method of claim 22, wherein the patient is ambulatory during the second predetermined period of time.

24. The method of claim 21, further comprising the device replacing the normal operating instructions with the temporary operating instructions and normally delivering therapy to the patient based on the formerly temporary operating instructions after the second predetermined period of time.

25. The method of claim 21, further comprising the device is not instructed to replace the normal operation instructions with the temporary operation instructions and normally deliver therapy to the patient based on the formerly temporary operation instructions, and the device reverting to delivery of therapy to the patient based on the normal operation instructions after the second predetermined period of time.

26. The method of claim 21, further comprising the repeater signaling the device to replace the normal instructions with the temporary instructions and normally provide therapy to the patient based on the formerly temporary instructions.

27. The method of claim 21, further comprising the repeater signaling the device to revert to delivery of therapy to the patient based on the normal operation instructions, and remove the temporary operation instructions from the second digital storage area.

28. The method of claim 21, further comprising the device sensing patient response to the therapy based on the temporary instructions and reverting to delivering therapy based on the normal instructions if the device senses an adverse response to the therapy based on the temporary instructions.

29. The method of claim 21, further comprising the device sensing patient response to the therapy based on the temporary operation instructions and, if the response is acceptable, replacing the normal instructions with the temporary operation instructions and delivering therapy to the patient based on the formerly temporary operation instructions.

30. The method of claim 21, further comprising the repeater receiving data from the device regarding patient response to therapy delivered based on the temporary instructions and communicating to the device to revert to delivering therapy based on the normal instructions if the patient response to therapy based on the temporary instructions is adverse.

31. The method of claim 21, further comprising the repeater receiving data from the device regarding patient response to therapy delivered based on the temporary operation instructions and, if the response is acceptable, signaling the device to replace the normal instructions with the temporary operation instructions and deliver therapy to the patient based on the formerly temporary operation instructions.

32. The method of claim 21, further comprising the patient signaling the device to revert to delivering therapy based on the normal operation instructions if the temporary operation instructions do not provide acceptable patient response.

33. The method of claim 32, wherein the patient signals the device using a magnet.

34. The method of claim 32, wherein the patient signals the patient with an electronic wand.

35. The method of claim 21, further comprising the device responding to a signal from the patient by replacing the normal operation instructions with the temporary operation instructions and delivering therapy to the patient based on the formerly temporary operation instructions.

36. The method of claim 35, further comprising the patient signaling the device to replace the normal instructions with the temporary operation instructions and deliver therapy to the patient based on the formerly temporary operation instructions using a magnet.

37. The method of claim 35, further comprising the patient signaling the device to replace the normal instructions with the temporary operation instructions and deliver therapy to the patient based on the formerly temporary operation instructions using an electronic wand.

38. The method of claim 21, further comprising the device responding to a signal from the caregiver by reverting to delivering therapy based on the normal operation instructions if the temporary operation instructions do not provide acceptable patient response.

39. The method of claim 38, wherein the caregiver signals the device to revert to delivering therapy based on the normal operation instructions using a magnet.

40. The method of claim 38, wherein the caregiver signals the device to revert to delivering therapy based on the normal operation instructions using an electronic wand.

41. The method of claim 32, further comprising the patient instructing the repeater to signal the device to revert to delivering therapy based on the normal instructions if the temporary instructions do not provide acceptable patient response.

42. A system for programming an implanted medical device comprising:
a medical device to be implanted within in a body of a patient, the medical device including electrical circuitry to provide treatment to the patient, a first digital storage area for holding normal operation instructions and settings, a second digital storage area for holding temporary operating instructions and settings, a communications subsystem and a timing subsystem;
a repeater for use external of the patient's body, the repeater including a communication subsystem configured to communicate with the communications subsystem of the medical device and with a programming device;
the implanted medical device configured to provide therapy to the patient using the normal operation instructions and settings stored in the first digital storage area;
the repeater configured to transmit temporary operation instructions and settings to the medical device for storage in the second digital storage area;
the repeater configured to instruct the medical device to use the temporary operating instructions and settings to deliver therapy to the patient;
wherein upon receiving from the repeater the instruction to use the temporary operating instructions and settings to deliver therapy to the patient, the medical device initiates a first predetermined period of time during which the medical device begins delivering therapy using the temporary operation instructions and settings, and wherein the medical device is configured to revert to delivering therapy using the normal operation instructions and settings if the medical device fails to receive a continuation signal from the repeater within a first time interval during the first predetermined period of time; and
wherein after the first predetermined period of time completes without reverting to normal operation, the medical device initiates a second predetermined period of time during which the patient is ambulatory and the medical device is configured to revert back delivering therapy using the normal operation instructions and settings if the medical device fails to receive a continuation signal from the repeater within a second time interval during the second predetermined period of time, wherein the second time interval is longer than the first time interval.

43. The system of claim 42, wherein the device is configured to replace the normal operation instructions with the temporary operation instructions and normally deliver therapy to the patient based on the formerly temporary operation instructions after the second predetermined period of time.

44. The system of claim 42, wherein the repeater is configured to signal the device to replace the normal instructions with the temporary operation instructions and normally deliver therapy to the patient based on the formerly temporary operation instructions.

45. The system of claim 42, wherein the device is configured to sense patient response to the therapy based on the temporary operation instructions and revert to delivering therapy based on the normal operation instructions if the device senses an adverse response to the therapy based on the temporary operation instructions.

46. The system of claim 42, wherein the repeater is configured to receive data from the device regarding patient response to therapy delivered based on the temporary operation instructions and communicating to the device to revert to delivering therapy based on the normal operation instructions if the patient response to therapy based on the temporary operation instructions is adverse.

47. The system of claim 42, wherein the device is configured to respond to the patient signaling the device by reverting to delivering therapy based on the normal operation instructions if the temporary operation instructions do not provide acceptable patient response.

48. The system of claim 47, wherein the patient signals the device to revert to delivering therapy based on the normal operation instructions using a magnet.

49. The system of claim 47, wherein the patient signals the device to revert to delivering therapy based on the normal operation instructions using an electronic wand.

50. A method of providing therapy to a patient wit a programmable implantable medical device, the method comprising:
providing the programmable implantable medical device and an external repeater;
delivering therapy with the device to the patient based on normal operating instructions stored in a first memory of the device;
communicating temporary operating instructions to the repeater;
communicating the temporary operating instructions to the device with the repeater;
storing the temporary operating instructions in a second memory of the device;
communicating to the device wit the repeater, instructing the device to begin delivering therapy to the patient based on the temporary operating instructions during a first predetermined period of time initiated by the device upon receiving from the repeater an instruction to use the temporary operating instructions and settings to deliver therapy to the patient;
reverting the device to delivering therapy to the patient based on the normal operating instructions if the device does not receive a continuation signal from the repeater within a first time interval during the first predetermined period of time;
while the patient is ambulatory, delivering therapy to the patient with the device based on the temporary operating instructions during a second predetermined period of time when the device receives a continuation signal from the repeater;
while the patient is ambulatory during the second predetermined period of time, reverting the device to delivering therapy to the patient based on the normal operating instructions if the device does not receive the continuation signal from the repeater within a second time interval during the second predetermined period of time, wherein the second time interval is longer than the first time interval.

51. The method of claim 50, further comprising the device replacing the normal operating instructions with the temporary operating instructions and normally delivering therapy to the patient based on the formerly temporary operating instructions after the second predetermined period of time.

52. The method of claim 50, further comprising the repeater signaling the device to replace the normal instructions with the temporary instructions and normally provide therapy to the patient based on the formerly temporary instructions.

53. The method of claim 50, further comprising the device sensing patient response to the therapy based on the temporary instructions and reverting to delivering therapy based on the normal instructions if the device senses an adverse response to the therapy based on the temporary instructions.

54. The method of claim 50, further comprising the repeater receiving data from the device regarding patient response to therapy delivered based on the temporary instructions and communicating to the device to revert to delivering therapy based on the normal instructions if the patient response to therapy based on the temporary instructions is adverse.

55. The method of claim 50, further comprising the patient signaling the device to revert to delivering therapy based on the normal instructions if the temporary instructions do not provide acceptable patient response.

56. The method of claim 55, wherein the patient signals the device using a magnet.

57. The method of claim 55, wherein the patient signals the patient with an electronic wand.

* * * * *

UNITED STATES PATENT AND TRADEMARK OFFICE
CERTIFICATE OF CORRECTION

| | | |
|---|---|---|
| PATENT NO. | : 7,460,912 B2 | Page 1 of 1 |
| APPLICATION NO. | : 10/993699 | |
| DATED | : December 2, 2008 | |
| INVENTOR(S) | : Hoyme et al. | |

It is certified that error appears in the above-identified patent and that said Letters Patent is hereby corrected as shown below:

In column 12, line 31, in Claim 50, delete "wit" and insert -- with --, therefor.

In column 12, line 46, in Claim 50, delete "wit" and insert -- with --, therefor.

Signed and Sealed this

Sixth Day of October, 2009

David J. Kappos
*Director of the United States Patent and Trademark Office*